(12) United States Patent
Hashimoto et al.

(10) Patent No.: US 8,767,916 B2
(45) Date of Patent: Jul. 1, 2014

(54) RADIATION IMAGING APPARATUS AND IMAGE PROCESSING METHOD

(71) Applicant: FUJIFILM Corporation, Tokyo (JP)

(72) Inventors: Atsushi Hashimoto, Ashigarakami-gun (JP); Takuji Tada, Ashigarakami-gun (JP); Dai Murakoshi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/057,836

(22) Filed: Oct. 18, 2013

(65) Prior Publication Data

US 2014/0044234 A1 Feb. 13, 2014

Related U.S. Application Data

(63) Continuation of application No. PCT/JP2012/059071, filed on Apr. 3, 2012.

(30) Foreign Application Priority Data

Apr. 20, 2011 (JP) .................................. 2011-093691
Dec. 2, 2011 (JP) .................................. 2011-264692

(51) Int. Cl.
  *G01N 23/04* (2006.01)
(52) U.S. Cl.
  USPC ........................................................ 378/62
(58) Field of Classification Search
  CPC ....... G01N 23/04; G01N 23/06; A61B 6/484; A61B 6/4291
  USPC ............................................................ 378/62
  See application file for complete search history.

(56) References Cited

U.S. PATENT DOCUMENTS 8,340,243 B2  12/2012  Ouchi et al.
2001/0030753 A1  10/2001  Ge

FOREIGN PATENT DOCUMENTS

JP    61-246601 A    11/1986
JP    2001-343208 A    12/2001
JP    2008-200361 A    9/2008
WO   WO 2010/050483 A1    5/2010

*Primary Examiner* — Jurie Yun
(74) *Attorney, Agent, or Firm* — Birch, Stewart, Kolasch & Birch, LLP

(57) ABSTRACT

An X-ray imaging apparatus comprises a first grid, a second grid, and an X-ray image detector. The first grid passes X-rays emitted from an X-ray source and produces a first periodic pattern image. The second grid opposes the first grid. The second grid partly blocks the first periodic pattern image and produces a second periodic pattern image with moiré fringes. The X-ray image detector detects the second periodic pattern image and produces image data. The X-ray image detector has pixels arranged in two dimensions in X and Y directions. The M pixels arranged in the Y direction form one group. The group is shifted in the Y direction by the number of the pixels less than M each time. A phase of an intensity modulated signal, composed of pixel values of the pixels in the each shifted group, is calculated. Thereby a differential phase image is produced.

17 Claims, 12 Drawing Sheets

US 8,767,916 B2

RADIATION IMAGING APPARATUS AND IMAGE PROCESSING METHOD

CROSS REFERENCE TO RELATED APPLICATIONS

This non-provisional application is a Continuation of International Application No. PCT/JP2012/059071 filed on Apr. 03, 2012, which claims the benefit of Japanese Patent Application Nos. 2011-093691 filed on Apr. 20, 2011 and 2011-264692 filed on Dec. 02, 2011, both are filed in Japan. The entire contents of all of the above applications are hereby incorporated by reference.

BACKGROUND OF THE INVENTION

1. Field of the Invention

The present invention relates to a radiation imaging apparatus for obtaining an image based on a phase shift of radiation and an image processing method for a radiation imaging apparatus.

2. Description Related to the Prior Art

Radiation, for example, X-rays have a characteristic that they attenuate depending on atomic number of an element constituting a substance and density and thickness of the substance. Due to this characteristic, the X-rays are used as a probe for inspecting inside of a subject in the fields of medical diagnoses and non-destructive inspections.

A common X-ray imaging apparatus comprises an X-ray source for emitting the X-rays and an X-ray image detector for detecting the X-rays. A subject is placed between the X-ray source and the X-ray image detector. The X-rays passed through the subject are imaged. To be more specific, the X-rays emitted from the X-ray source to the X-ray image detector are absorbed by the subject while passing through the subject and thereby attenuated. Then the X-rays are incident on the X-ray image detector. Hence, the X-ray image detector detects an image produced based on intensity changes of the X-rays caused by the subject.

The smaller the atomic number of the element, the lower the X-ray absorption power. Because the intensity changes of the X-rays caused by living soft tissue and soft matter are small, their images do not have sufficient contrast. For example, an articular cartilage of a human joint and its surrounding synovial fluid are composed mostly of water. A difference in X-ray absorption power between the cartilaginous part and the synovial fluid is small, resulting in poor contrast of the image.

Against this backdrop, recently, X-ray phase contrast imaging has been researched actively. The X-ray phase contrast imaging is a technique to image the phase shifts of the X-rays passing through the subject, based on the fact that the phase shifts are greater than the intensity changes. Thereby a high contrast image of the subject with low X-ray absorption power can be obtained.

An X-ray imaging apparatus for performing the above-described X-ray phase contrast imaging is suggested. In this X-ray imaging apparatus, first and second grids are arranged parallel with each other at a given interval, between an X-ray source and an X-ray image detector (for example, see Japanese Patent Laid-Open Publication No. 2008-200361). In this X-ray imaging apparatus, an X-ray image detector captures a moiré image of the X-rays emitted from the X-ray source and passed through the first and second grids. Thereby, a phase contrast image is obtained.

The X-ray imaging apparatus disclosed in the Japanese Patent Laid-Open Publication No. 2008-200361 utilizes a fringe scanning method. In the fringe scanning method, the second grid is moved intermittently relative to the first grid at predetermined regular intervals smaller than a grid pitch in a direction substantially perpendicular to a grid direction. The moiré images are obtained by capturing a moiré image each time the second grid halts. Based on the moiré images, an amount of the phase shift of the X-rays, caused by interaction with the subject, is detected and a differential phase image is produced. A phase contrast image is produced by performing an integrating process on the differential phase image.

The fringe scanning method requires a moving mechanism with high precision to move the first or second grid accurately at a pitch smaller than its grid pitch. This makes the apparatus complex and incurs high cost. The fringe scanning method requires to perform several image captures to produce the single phase contrast image. The motions of the subject and the grids during the series of image captures may degrade image quality of the differential phase image. The Japanese Patent Laid-Open Publication No. 2008-200361 suggests producing a differential phase image from a single moiré image obtained by a single image capture without moving the first and second grids, but a specific method is not disclosed.

U.S. Pat. No. 8,340,243 (corresponding to WO2010/050483) suggests a Fourier transform method. In this method, a moiré image is obtained by a single image capture without moving the first and second grids. Then, the moiré image is subjected to a series of processes: Fourier transform, extraction of a spectrum corresponding to a carrier frequency, and inverse Fourier transform. Thereby, a differential phase image is obtained.

In the Fourier transform method disclosed in U.S. Pat. No. 8,340,243, a peak position of a carrier frequency component cannot be obtained accurately because the distortion in the moiré fringes of the moiré image in a direction of a period or fringes, due to distortion, an arrangement error, or the like of the first and second grids, spreads the carrier frequency, and this causes a degradation of the image quality of the differential phase image.

In the Fourier transform method disclosed in the U.S. Pat. No. 8,340,243, the moiré image is transformed into a frequency space image by using the Fourier transform. Hence, the resolution in the frequency space decreases and the image quality of the differential phase image degrades when the X-ray image detector has a small number of pixels.

In the X-ray imaging apparatus disclosed in the U.S. Pat. No. 8,340,243, the positions of the first and second grids need to be adjusted with high precision and an X-ray image detector with a large number of pixels needs to be used so as to obtain uniform moiré fringes without distortion in period or direction to improve image quality of the differential phase image.

SUMMARY OF THE INVENTION

An object of the present invention is to provide a radiation imaging apparatus and an image processing method capable of producing a differential phase image with high image quality from a single moiré image.

In order to achieve the above objects, the radiation imaging apparatus of the present invention comprises a radiation source for emitting radiation, a first grid, a second grid, a radiation image detector, and a differential phase image generator. The first grid passes the radiation and produces a first periodic pattern image. The second grid partly blocks the first periodic pattern image to produces a second periodic pattern image with moiré fringes. The radiation image detector detects the second periodic pattern image with the use of pixels, arranged in two dimensions, and produces image data. The differential phase image generator groups the M pixels, arranged in a predetermined direction, as a group. The differential phase image generator calculates a phase of an intensity modulated signal, with the group shifted in the predetermined direction by the number of the pixels less than M each time. Thereby the differential phase image generator produces a differential phase image. The intensity modulated signal is composed of pixel values of the pixels in the each group.

It is preferable that the differential phase image generator calculates the phase of the intensity modulated signal, with the group shifted in the predetermined direction by the one pixel each time. The intensity modulated signal is composed of the pixel values of the pixels in the each group.

It is preferable that the predetermined direction is a direction substantially orthogonal to the moiré fringes. In this case, it is preferable that the number of the pixels constituting the group corresponds to an integral multiple of a period of the moiré fringes. It is preferable that the number of the pixels constituting the group corresponds to the one period of the moiré fringes. The number of the pixels constituting the group may be less than the number of the pixels corresponding to one period of the moiré fringes.

It is preferable that the moiré fringes are produced by arranging the second grid with a tilt in a direction within a grid surface relative to the first grid. It is preferable that the moiré fringes are substantially orthogonal to grid directions of the first and second grids.

The moiré fringes are produced by adjusting a positional relation between the first and second grids in an opposing direction or adjusting a grid pitch or grid pitches of the first and second grids. The moiré fringes may be substantially parallel with a grid direction of the first and second grids.

The moiré fringes are produced by arranging the second grid with a tilt in a direction within a grid surface relative to the first grid and adjusting a positional relation between the first and second grids in an opposing direction or adjusting a grid pitch or grid pitches of the first and second grids. The moiré fringes may be neither orthogonal nor parallel to grid directions of the first and second grids.

It is preferable that the radiation imaging apparatus further comprises a phase contrast image generator. The phase contrast image generator performs an integrating process on the differential phase image in a direction substantially orthogonal to a grid direction or grid directions of the first and second grids. Thereby the phase contrast image generator produces a phase contrast image.

It is preferable that the radiation imaging apparatus further comprises correction image storage and a correction processor. The correction image storage stores a differential phase image, produced by the differential phase image generator in the absence of a subject, as a correction image. The correction processor subtracts the correction image, stored in the correction image storage, from a differential phase image produced by the differential phase image generator in the presence of the subject. In this case, it is preferable that the radiation imaging apparatus further comprises a phase contrast image generator. The phase contrast image generator performs an integrating process on a corrected differential phase image, corrected by the correction processor, in a direction substantially orthogonal to a grid direction or grid directions of the first and second grids and produces a phase contrast image.

It is preferable that the first grid is an absorption grid for projecting the incident radiation in a geometrical-optical manner to the second grid and producing the first periodic pattern image.

The first grid may be an absorption grid or a phase grid for allowing the incident radiation to cause Talbot effect and producing the first periodic pattern image.

It is preferable that the radiation imaging apparatus further comprises a multi-slit for partly blocking the radiation emitted from the radiation source and dispersing a focus.

The radiation image detector may be a radiation image detector of an optical reading system in which a charge is read out from each pixel by scanning a linear reading light source in the predetermined direction and image data is produced, and the linear reading light source extends in a direction orthogonal to the predetermined direction.

The image processing method of the present invention is used for a radiation imaging apparatus comprising a radiation source for emitting radiation, a first grid, a second grid, and a radiation image detector. The first grid passes the radiation and produces a first periodic pattern image. The second grid partly blocks the first periodic pattern image to produce a second periodic pattern image with moiré fringes. The radiation image detector detects the second periodic pattern image with the use of pixels, arranged in two dimensions, and produces image data. In this image processing method, the M pixels arranged in a predetermined direction are grouped as a group. A phase of an intensity modulated signal is calculated, with the group shifted in the predetermined direction by the number of the pixels less than the M each time. Thereby a differential phase image is produced. The intensity modulated signal is composed of pixel values of the pixels in the each group.

According to the present invention, the M pixels arranged in the predetermined direction are grouped as a group. The pixel values of the pixels in the each group constitute the intensity modulated signal. The phase of the intensity modulated signal is calculated, with the group shifted in the predetermined direction by the number of the pixels less than the M each time. Thereby the differential phase image is produced. The differential phase image with high image quality is produced from the single moiré image detected by the radiation image detector.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS (First Embodiment)

Figure 1:
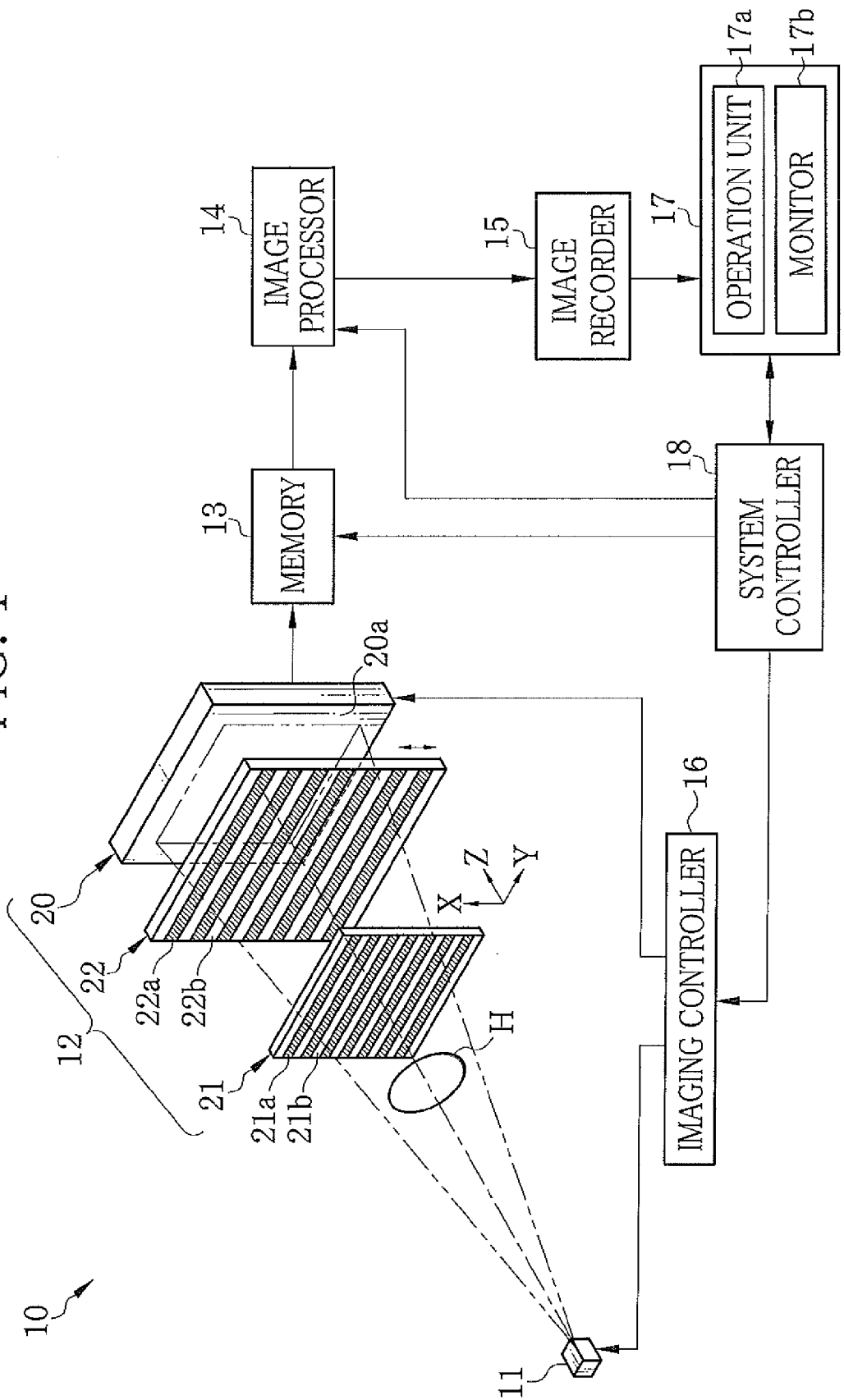
FIG. 1 is a schematic view illustrating configuration of an X-ray imaging apparatus.

In FIG. 1, an X-ray imaging apparatus 10 comprises an X-ray source 11, an imaging unit 12, a memory 13, an image processor 14, an image recorder 15, an imaging controller 16, a console 17, and a system controller 18. As is well known, the X-ray source 11 has a rotating anode type X-ray tube (not shown) and a collimator (not shown) for restricting an X-ray emission field. The X-ray source 11 emits X-rays to a subject H.

The imaging unit 12 comprises an X-ray image detector 20, a first grid 21, and a second grid 22. The first and second grids 21 and 22 are absorption grids and disposed to oppose the X-ray source 11 relative to a Z direction, being an X-ray emission direction. There is a space enough to place the subject H between the X-ray source 11 and the first grid 21. The X-ray image detector 20 is a flat panel detector using a semiconductor circuit. The X-ray image detector 20 is disposed behind and close to the second grid 22. A detection surface 20a of the X-ray image detector 20 is in an X-Y plane orthogonal to the Z direction.

A grid surface of the first grid 21 is in the X-Y plane. A plurality of X-ray absorbing portions 21a and a plurality of X-ray transmitting portions 21b are formed in the grid surface. The X-ray absorbing portions 21a and the X-ray transmitting portions 21b extend in a Y direction (grid direction). The X-ray absorbing portions 21a and the X-ray transmitting portions 21b are arranged alternately in an X direction and form a stripe-like pattern. The second grid 22 comprises a plurality of X-ray absorbing portions 22a and a plurality of X-ray transmitting portions 22b. The X-ray absorbing portions 22a and the X-ray transmitting portions 22b extend in the Y direction and are arranged alternately in the X direction, in a manner similar to the first grid 21. The X-ray absorbing portions 21a and 22a are formed of metal such as gold (Au) or platinum (Pt) having X-ray absorption properties. The X-ray transmitting portions 21b and 22b are formed of an X-ray transmissive material such as silicon (Si) or polymer, or a gap.

The first grid 21 passes a part of the X-rays, emitted from the X-ray source 11, to produce a first periodic pattern image (hereinafter referred to as the G1 image). The second grid 22 passes a part of the G1 image, produced by the first grid 21, to produce a second periodic pattern image (hereinafter referred to as the G2 image). The G1 image substantially coincides with a grid pattern of the second grid 22. The first grid 21 is slightly tilted, relative to the second grid 22, around a Z axis (a direction within the grid surface). Moiré fringes occur in the G2 image.

The moiré fringes have a period in accordance with a tilt angle. The X-ray image detector 20 detects the G2 image to produce image data. The memory 13 temporarily stores the image data read out from the X-ray image detector 20. The image processor 14 produces a differential phase image based on the image data stored in the memory 13. The image processor 14 produces a phase contrast image based on the differential phase image. The image recorder 15 records the differential phase image and the phase contrast image produced by the image processor 14. The imaging controller 16 controls the X-ray source 11 and the imaging unit 12.

The console 17 comprises an operation unit 17a and a monitor 17b. The operation unit 17a allows operations such as setting imaging conditions, switching an imaging mode, and commanding execution of imaging. The monitor 17b displays imaging information, the differential phase image, the phase contrast image, or the like. Imaging modes include a preliminary imaging mode and a main imaging mode. In the preliminary imaging mode, preliminary imaging is performed in the absence of the subject H. In the main imaging mode, main imaging is performed in the presence of the subject H. The system controller 18 performs centralized control of each section in accordance with a signal inputted from the operation unit 17a.

Figure 2:
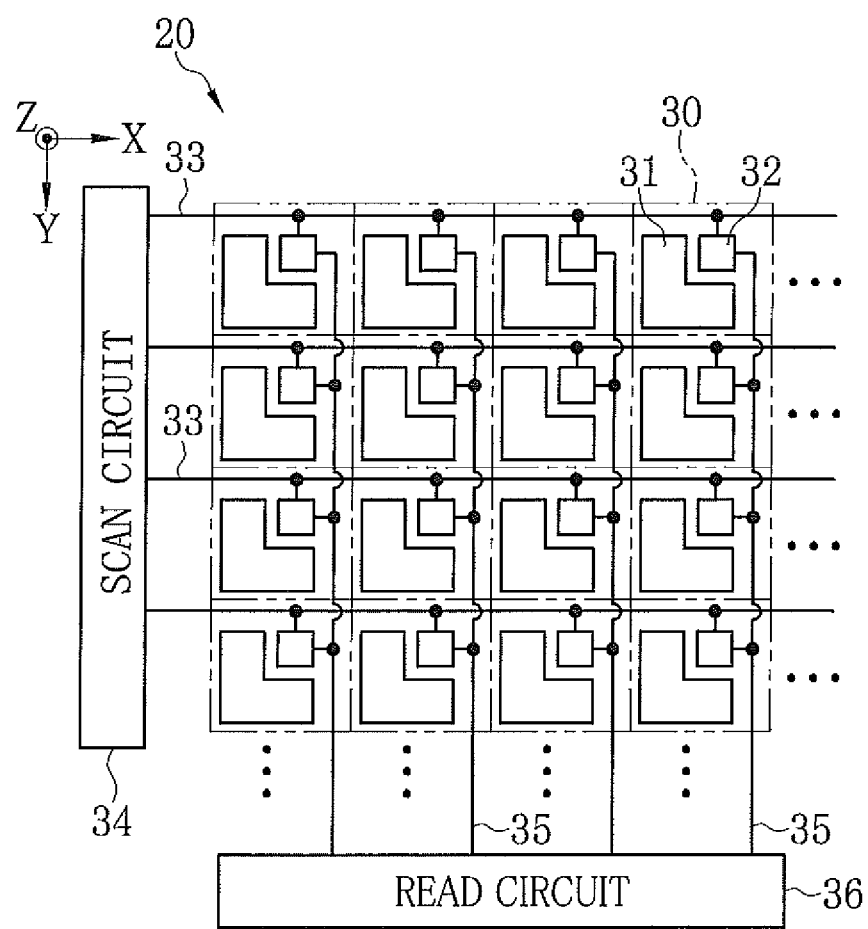
FIG. 2 is a schematic view illustrating configuration of an X-ray image detector.

In FIG. 2, the X-ray image detector 20 is composed of a plurality of pixels 30 arranged in two dimensions, gate scanning lines 33, a scan circuit 34, signal line 35, and a read circuit 36. The pixel 30 comprises a pixel electrode 31 and a TFT (Thin Film Transistor) 32 as is well known. The pixel electrode 31 collects a charge generated by the incident X-rays in a semiconductor film such as amorphous selenium (a-Se). The TFT 32 reads the charge collected by the pixel electrode 31. The gate scanning line 33 is provided to each line of the pixels 30. The scan circuit 34 applies a scan signal to each gate scanning line 33. The scan signal turns the TFT 32 on/off. The signal line 35 is provided to each column of the pixels 30. The read circuit 36 reads the charges from the pixels 30 through the signal lines 35, converts the charges into image data, and outputs the image data. Note that a layer configuration of each pixel 30 is similar to that disclosed in Japanese Patent Laid-Open Publication 2002-26300.

The read circuit 36 is composed of an integrating amplifier, an A/D converter, a correction circuit (all not shown), and the like as is well known. The integrating amplifier integrates the charges, outputted from the respective pixels 30 through the signal line 35, to produce an image signal. The A/D converter coverts the image signal, produced by the integrating amplifier, into digital image data. The correction circuit performs dark current correction, gain correction, linearity correction, or the like on the image data. The correction circuit inputs corrected image data to the memory 13.

The X-ray image detector 20 is not limited to a direct conversion type that directly converts the incident X-rays into charges. The X-ray image detector 20 may be an indirect conversion type. The indirect conversion type converts the incident X-rays into light photons with the use of a scintillator such as cesium iodide (CsI) or gadolinium oxysulfide (GOS). A photodiode converts the light photons into charges. The X-ray image detector 20 is not limited to a radiation image detector which uses a TFT panel. A radiation image detector which uses a solid state image sensor such as a CCD sensor or a CMOS sensor may be used.

Figure 3:
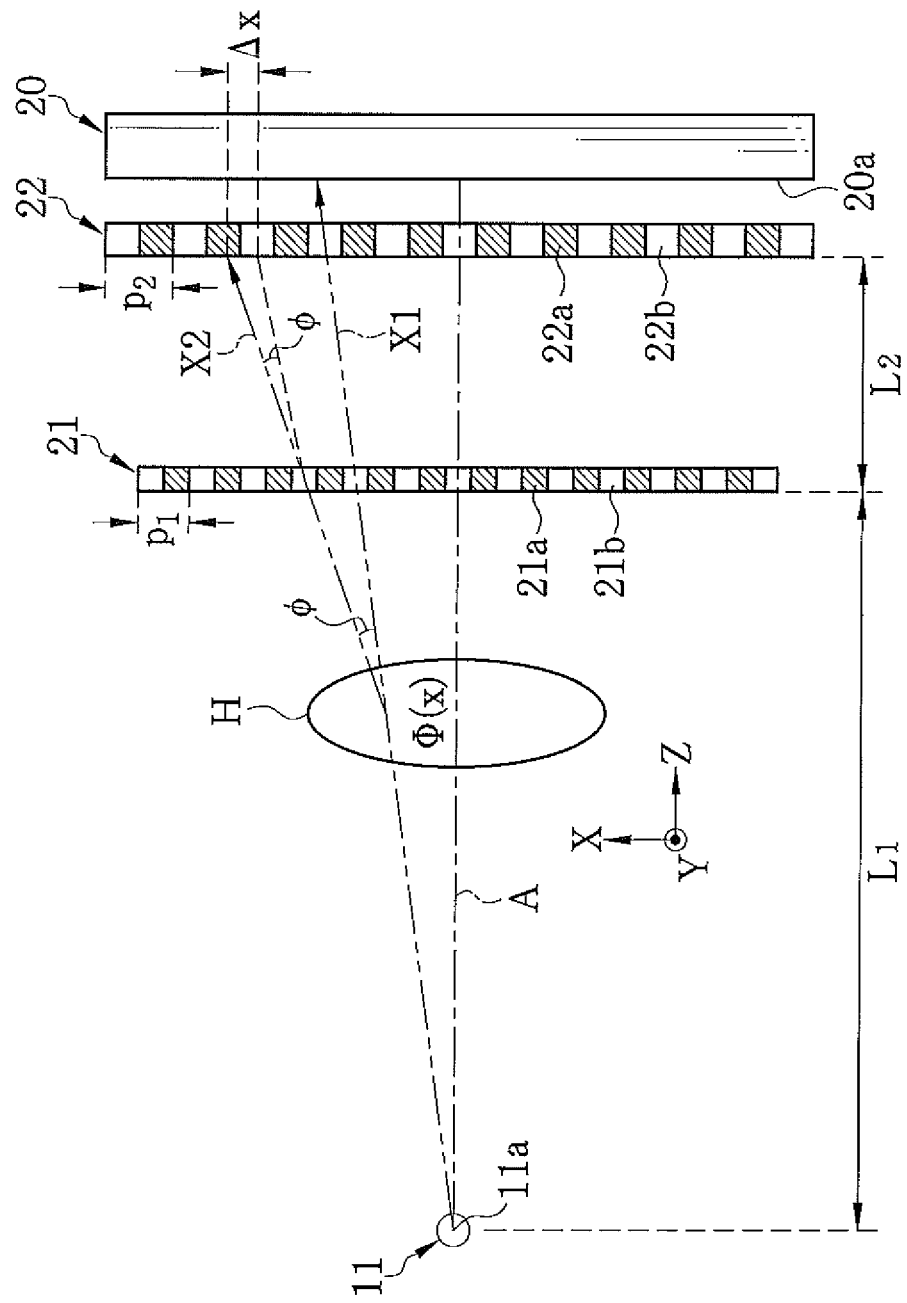
FIG. 3 is an explanatory view illustrating a configuration of a first grid and a second grid.

In FIG. 3, the X-rays emitted from the X-ray source 11 are cone-shaped beams having an X-ray focal point 11a as an X-ray emission point. The first grid 21 is configured to project the X-rays, passed through the X-ray transmitting portions 21b, in a substantially geometrical-optical manner. To be more specific, the width of the X-ray transmitting portion 21b in the X direction is sufficiently larger than an effective wavelength of the X-rays from the X-ray source 11. The X-ray transmitting portion 21b passes most of the X-rays linearly without diffraction. For example, when the rotating anode of the X-ray source 11 is made from tungsten and the tube voltage is 50 kV, the effective wavelength of the X-rays is approximately 0.4 Å. In this case, the width of the X-ray transmitting portion 21b is approximately from 1 μm to 10 μm. Note that the second grid 22 is configured in a similar manner.

The G1 image produced by the first grid 21 is enlarged in proportion to a distance from the X-ray focal point 11a. The grid pitch $p_2$ the second grid 22 is determined to coincide with the periodic pattern of the G1 image at the position of the second grid 22. To be more specific, the grid pitch $p_2$ of the second grid 22 is determined to substantially satisfy a mathematical expression (1) below, where $p_1$ denotes a grid pitch of the first grid 21, $L_1$ denotes a distance between the X-ray focal point 11a and the first grid 21, and $L_2$ denotes a distance between the first grid 21 and the second grid 22.

$$p_2 = \frac{L_1 + L_2}{L_1} p_1 \tag{1}$$

When the subject H is disposed between the X-ray source 11 and the first grid 21, the G2 image is modulated by the subject H. An amount of the modulation reflects a refraction angle of the X-rays caused by the subject H.

Next, a method for producing the differential phase image is described. Here, x, y, and z denote coordinates in the X, Y, and Z directions, respectively. FIG. 3 shows a path of the X-rays refracted in accordance with phase shift distribution $\Phi(x)$ of the subject H by way of example. A character X1 denotes a path of the X-rays in the absence of the subject H. The X-rays of the path X1 pass through the first and second grids 21 and 22 and are incident on the X-ray image detector 20. In the presence of the subject H, a character X2 denotes a path of the X-rays refracted by the subject H. The X-rays of the path X2 pass through the first grid 21 and then absorbed by the X-ray absorbing portion 22a of the second grid 22.

The phase shift distribution $\Phi(x)$ of the subject H is represented by a mathematical expression (2) below, where n(x, z) denotes the refractive index distribution of the subject H. Here, y coordinate is omitted for the sake of simplifying the description.

$$\Phi(x) = \frac{2\pi}{\lambda} \int [1 - n(x, z)] dz \tag{2}$$

Due to the refraction of the X-rays caused by the subject H, the G1 image formed at the position of the second grid 22 is displaced in the X direction by an amount corresponding to the refraction angle ϕ. A displacement amount Δx is approximately represented by a mathematical expression (3) below, based on the fact that the refraction angle ϕ of the X-rays is minute.

$$\Delta x \approx L_2 \phi \tag{3}$$

Here, the refraction angle ϕ is represented by a mathematical expression (4) using a wavelength λ of the X-rays and the phase shift distribution $\Phi(x)$ of the subject H.

$$\phi = \frac{\lambda}{2\pi} \frac{\partial \Phi(x)}{\partial x} \tag{4}$$

Thus the displacement amount Δx relates to the phase shift distribution $\Phi(x)$ of the subject H. The displacement amount Δx and the refraction angle ϕ relate to a phase shift amount ψ of an intensity modulated signal of each pixel detected by the X-ray image detector 20, in a manner shown by a mathematical expression (5). The phase shift value ψ is a value of the phase shift of the intensity modulated signal between the presence of the object H and the absence of the object H. Here, the intensity modulated signal is a waveform signal representing changes in intensity of the pixel value caused by positional changes of the first grid 21 and the second grid 22.

$$\psi = \frac{2\pi}{p_2} \Delta x \tag{5}$$
$$= \frac{2\pi}{p_2} L_2 \phi$$

The mathematical expressions (4) and (5) show that the phase shift value ψ of the intensity modulated signal corresponds to a differential value of the phase shift distribution $\Phi(x)$. The differential value is integrated with respect to x. Thereby the phase shift distribution $\Phi(x)$, that is, the phase contrast image is produced.

Figure 4:
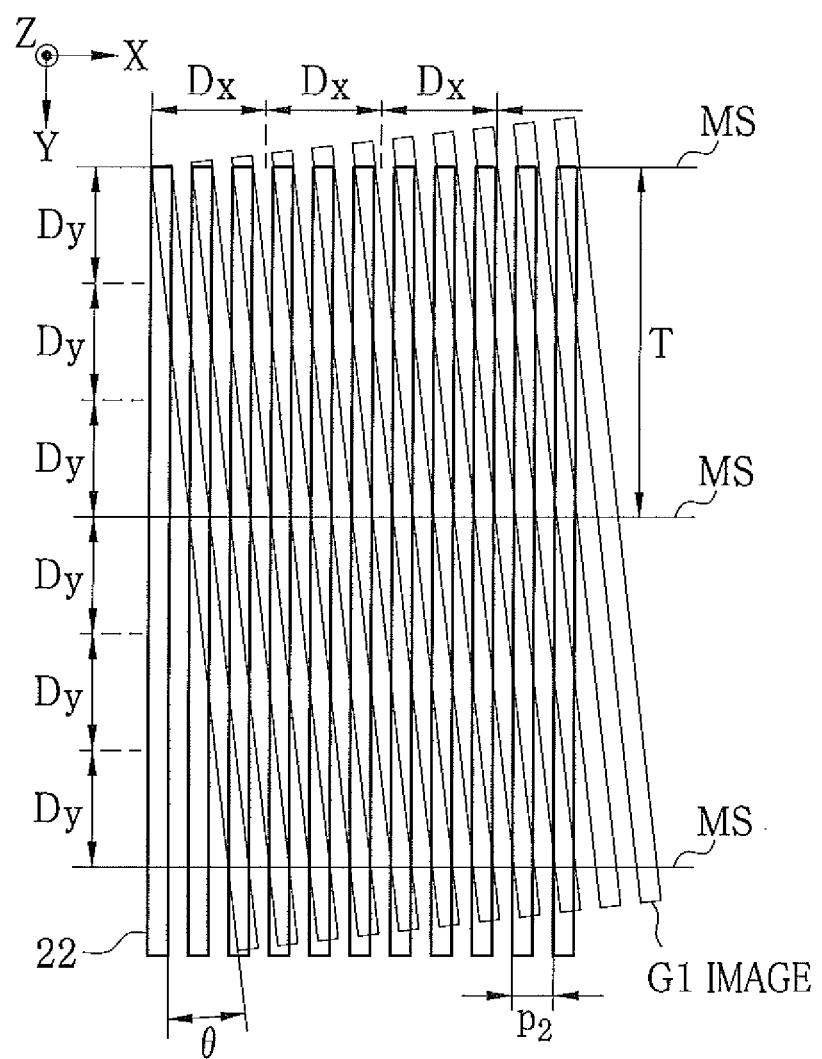
FIG. 4 is an explanatory view illustrating a positional relation between the first and second grids relative to pixels of the X-ray image detector.

In FIG. 4, the first grid 21 is tilted relative to the second grid 22 by an angle θ around the Z axis such that the G1 image is tilted relative to the second grid 22 by the angle θ around the Z axis. Thereby moiré fringes MS occur in the G2 image. The moiré fringes MS have a period (hereinafter referred to as the moiré period) T substantially in the Y direction. The moiré period T is represented by a mathematical expression (6) below.

$$T = \frac{p_2}{\tan\theta} \tag{6}$$

"Dx" (hereinafter referred to as the main pixel size Dx) denotes the size of the pixel 30 in the X-direction of the X-ray image detector 20. "Dy" (hereinafter referred to as the sub-pixel size Dy) denotes the size of the pixel 30 in the Y direction. The tilt angle θ of the second grid 22 is determined such that the moiré period T substantially equals an integral multiple of the sub-pixel size Dy.

Figure 5:
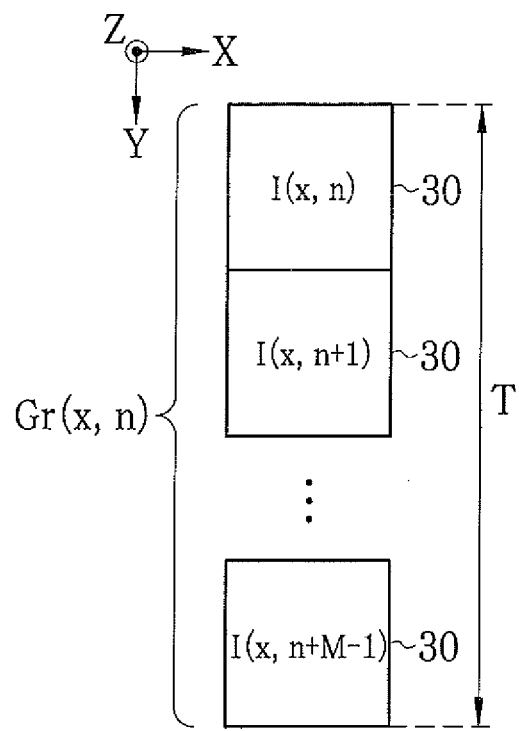
FIG. 5 is an explanatory view illustrating a group of the pixels constituting the intensity modulated signal.

In FIG. 5, the M pixels 30 arranged in the Y direction are grouped as a group Gr(x, n). Here, "M" is a positive integer, and "n" is a positive integer. The "n" denotes the y coordinate of the first pixel 30 in the group Gr(x, n). In this embodiment, the number M of the pixels in one group Gr(x, n) is the same as the number ν (in an example in FIG. 4, ν=3) of the pixels included in one moiré period T.

Figure 6:
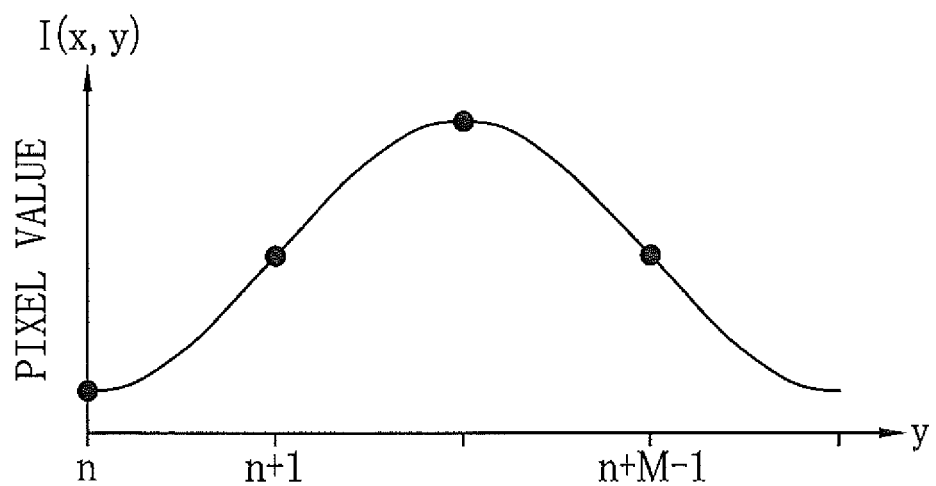
FIG. 6 is a graph illustrating an intensity modulated signal.

"I(x, y)" denotes the pixel value of the pixel 30 at the coordinates (x, y). The pixel value I(x, y) is obtained from the image data stored in the memory 13. As shown in FIG. 6, the amount of the intensity modulation of the G1 image caused by the second grid 22 differs depending on the y coordinate of the pixel 30 so that the pixel values I(x, n) to I(x, n+M−1) in one group Gr(x, n) constitute the intensity modulated signal of one period. Hence, the pixel values I(x, n) to I(x, n+M−1) in one group Gr(x, n) correspond to the intensity modulated signal of one period obtained while the first or second grid is moved by a predetermined amount each time in a direction (X direction) substantially perpendicular to the grid direction in a conventional fringe scanning method.

Figure 7:
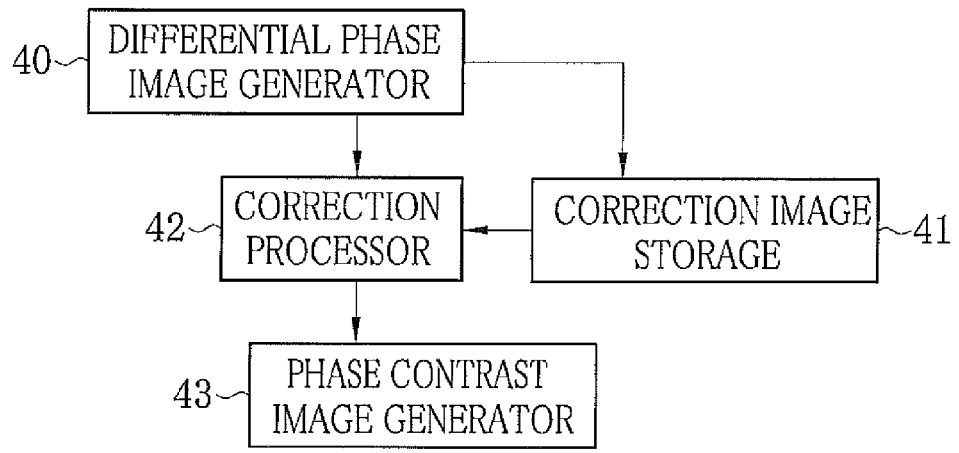
FIG. 7 is a block diagram illustrating configuration of an image processor.

In FIG. 7, the image processor 14 comprises a differential phase image generator 40, correction image storage 41, a correction processor 42, and a phase contrast image generator 43. The differential phase image generator 40 reads each image data, obtained from the preliminary imaging and the main imaging and stored in the memory 13, and produces a differential phase image with the use of a method described below. The correction image storage 41 stores the differential phase image, produced by the differential phase image generator 40 at the time of the preliminary imaging, as a correction image. The correction processor 42 subtracts the correction image, stored in the correction image storage 41, from the differential phase image produced by the differential phase image generator 40 at the time of the main imaging. Thereby, the correction processor 42 produces a corrected differential phase image. The phase contrast image generator 43 performs an integrating process on the corrected differential phase image in the X direction to produce the phase contrast image.

Figure 8:
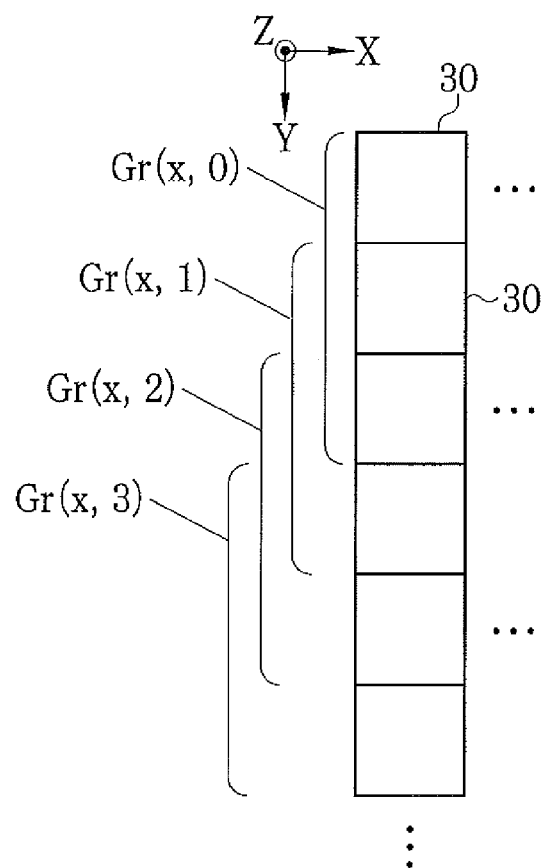
FIG. 8 is an explanatory view illustrating how to shift a group when a differential phase value is calculated.

As shown in FIG. 8, the differential phase image generator 40 calculates a differential phase value based on the intensity modulated signal of each group Gr(x, n), with the group Gr(x, n) shifted (with "n" incremented) in the Y direction by one pixel each time in each column of the pixels 30. The columns of the pixels 30 are arranged in the X-direction. The differential phase image is obtained by calculating the differential phase value for each pixel 30.

The differential phase value is calculated in a manner similar to the fringe scanning method. To be more specific, a method for calculating phase distribution in a phase modulation interference method (fringe scanning interference method) disclosed in "Applied Optics—Introduction to Optical Measurement" (T. Yatagai, published by Maruzen, pages 136 to 138) is used.

The differential phase image generator 40 calculates a determinant (7) below, and applies a calculation result to a mathematical expression (8). Thereby, the differential phase image generator 40 obtains the differential phase value $\psi(x, y)$.

$$a = A^{-1}(\delta_k) B(\delta_k) \tag{7}$$

$$\psi(x, n) = -\tan^{-1} \frac{a_2}{a_1} \tag{8}$$

A reference phase $\delta_k$, matrices "a", $A(\delta_k)$, and $B(\delta_k)$ are represented by respective mathematical expressions (9) to (12) below.

$$\delta_k = 2\pi \frac{k}{v} \tag{9}$$

$$a = \begin{pmatrix} a_0 \\ a_1 \\ a_2 \end{pmatrix} \tag{10}$$

$$A(\delta_k) = \begin{pmatrix} 1 & \frac{1}{M}\sum_{k=0}^{M-1}\cos\delta_k & \frac{1}{M}\sum_{k=0}^{M-1}\sin\delta_k \\ \frac{1}{M}\sum_{k=0}^{M-1}\cos\delta_k & \frac{1}{M}\sum_{k=0}^{M-1}\cos^2\delta_k & \frac{1}{M}\sum_{k=0}^{M-1}\cos\delta_k\sin\delta_k \\ \frac{1}{M}\sum_{k=0}^{M-1}\sin\delta_k & \frac{1}{M}\sum_{k=0}^{M-1}\cos\delta_k\sin\delta_k & \frac{1}{M}\sum_{k=0}^{M-1}\sin^2\delta_k \end{pmatrix} \tag{11}$$

$$B(\delta_k) = \begin{pmatrix} \frac{1}{M}\sum_{k=0}^{M-1} I(x, n+k) \\ \frac{1}{M}\sum_{k=0}^{M-1} I(x, n+k)\cos\delta_k \\ \frac{1}{M}\sum_{k=0}^{M-1} I(x, n+k)\sin\delta_k \end{pmatrix} \tag{12}$$

In this embodiment, because M equals v (M=v), the reference phase $\delta_k$ gradually changes at regular intervals between 0 to $2\pi$.

In this case, a non-diagonal term of the matrix $A(\delta_k)$ is 0, and a diagonal term other than 1 is ½. Hence, the differential phase value $\psi(x, y)$ is calculated using a simple mathematical expression (13).

$$\psi(x, n) = -\tan^{-1} \frac{\sum_{k=0}^{M-1} I(x, n+k)\sin\delta_k}{\sum_{k=0}^{M-1} I(x, n+k)\cos\delta_k} \tag{13}$$

Next, an operation of the above-configured X-ray imaging apparatus 10 is described. First, when a command for preliminary imaging is inputted from the operation unit 17a in the absence of the subject H, the X-ray source 11 emits the X-rays. The X-ray image detector 20 detects the G2 image and produces the image data. The image data is stored in the memory 13. Then, the image processor 14 reads out the image data from the memory 13. In the image processor 14, the differential phase image generator 40 performs the above-described calculation, based on the image data, to produce the differential phase image. The differential phase image, being the correction image, is stored in the correction image storage 41. Thereby the preliminary imaging is ended.

Then, the subject H is placed between the X-ray source 11 and the first grid 21. When a command for the main imaging is inputted from the operation unit 17a, the X-ray source 11 emits the X-rays, and the X-ray image detector 20 detects the G2 image and produces the image data in a manner similar to the above. The image data is stored in the memory 13. Then, the image processor 14 reads out the image data from the memory 13. In the image processor 14, the differential phase image generator 40 performs the above-described calculation, based on the image data, to produce the differential phase image of the main imaging.

The differential phase image of the main imaging is inputted to the correction processor 42. The correction processor 42 reads out the correction image (the differential phase image of the preliminary imaging) from the correction image storage 41, and subtracts the correction image from the differential phase image of the main imaging. Thereby, the corrected differential phase image, reflecting or carrying only the phase information of the subject H, is produced. The corrected differential phase image is inputted to the phase contrast image generator 43, and then subjected to the integrating process in the X direction. Thereby, the phase contrast image is produced.

The phase contrast image and the corrected differential phase image are stored in the image recorder 15, and then inputted to the console 17 and displayed on the monitor 17b.

As described above, in this embodiment, the differential phase value is calculated, with the group Gr(x, n) shifted in the Y direction by one pixel each time. Hence, the differential phase image has the same number of pixels in the X and Y directions.

Figure 9:
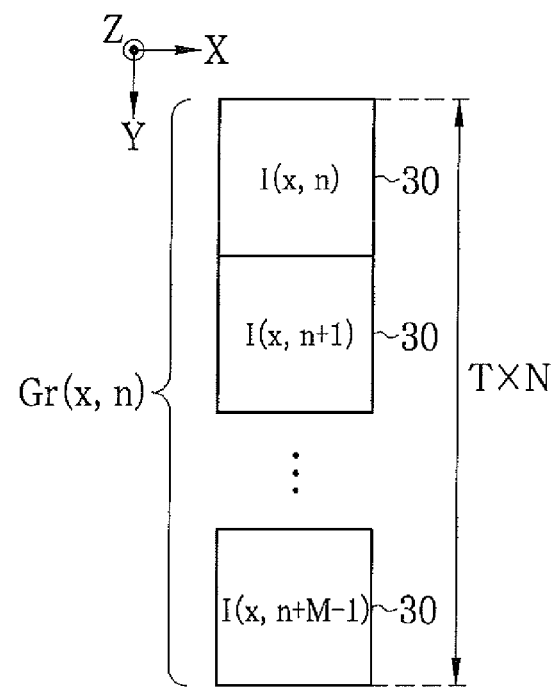
FIG. 9 is an explanatory view illustrating a first modified example of how to form a group.
Figure 10:
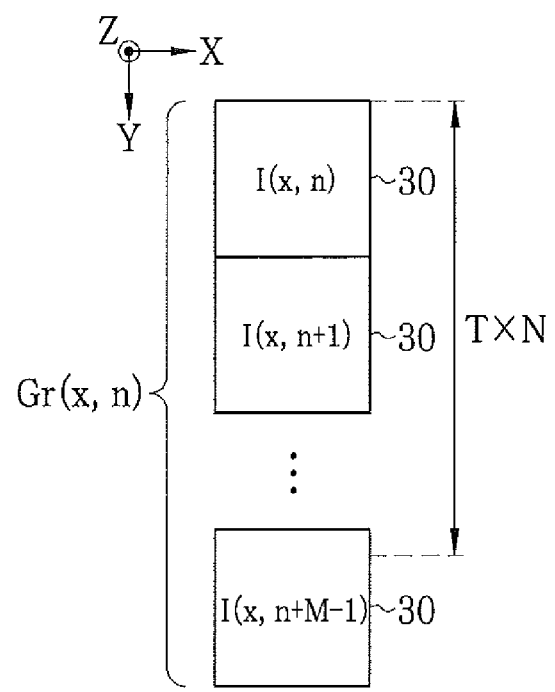
FIG. 10 is an explanatory view illustrating a second modified example of how to form a group.

In the above-described first embodiment, as shown in FIG. 5, note that the number M of the pixels in one group Gr(x, n) is equivalent to the number ν of the pixels included in the single moiré period T. Alternatively, as shown in FIG. 9, the number M of the pixels in one group Gr(x, n) may be equivalent to a product of N (an integer of two or more) times the number ν of the pixels included in the single moiré period T.

Figure 14:
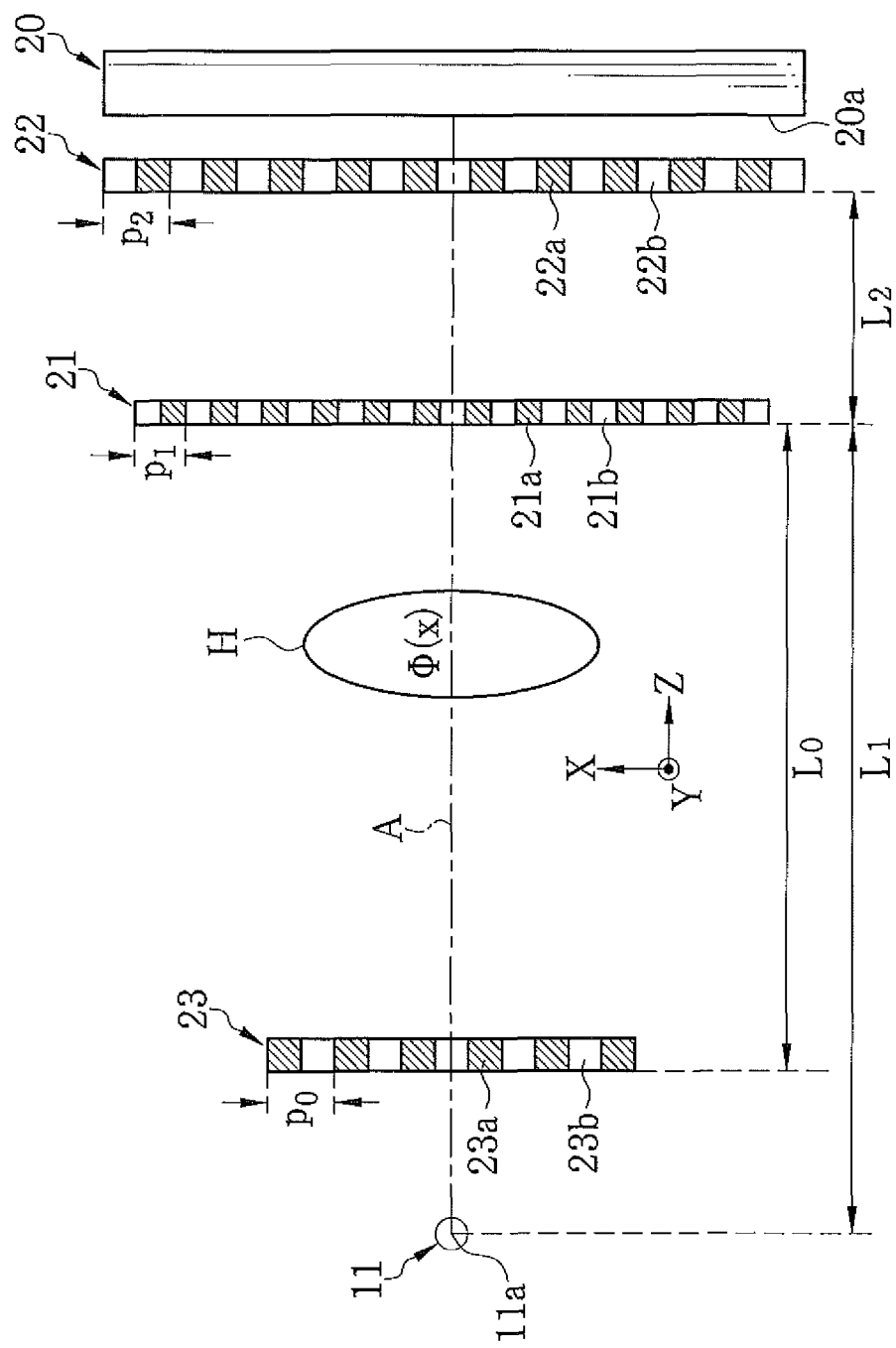
FIG. 14 is an explanatory view illustrating configuration of the X-ray imaging apparatus with a multi-slit according to a third embodiment.

As shown in FIG. 14, the number M of the pixels in one group Gr(x, n) may not be equivalent to the number ν of the pixels included in the single moiré period T or N times the moiré period T. In this case, the mathematical expression (13) cannot be used for calculating the differential phase value $\psi(x, y)$. Instead, the calculation result of the determinant (7) is applied to the mathematical expression (8) to obtain the differential phase value $\psi(x, y)$.

Figure 11:
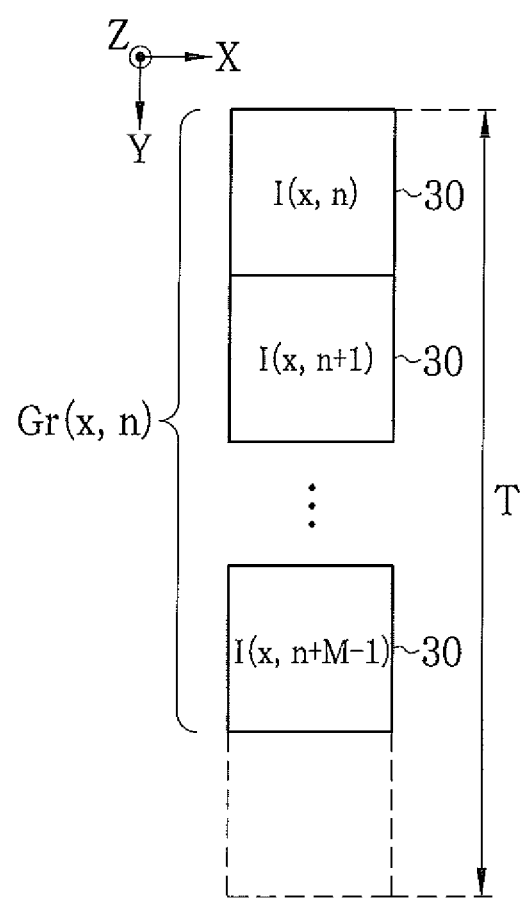
FIG. 11 is an explanatory view illustrating a third modified example of how to form a group.

As shown in FIG. 11, the Number M of the pixels in one group Gr(x, n) may be less than the number ν of the pixels included in the single moiré period T. Also in this case, the mathematical expression (13) cannot be used for calculating the differential phase value $\psi(x, y)$. Instead, the calculation result of the determinant (7) is applied to the mathematical expression (8) to obtain the differential phase value $\psi(x, y)$. Because the small number of pixels is used to calculate the differential phase value, the S/N ratio is less than that in the first embodiment, but the resolution improves.

In the first embodiment, as shown in FIG. 8, the differential phase value is calculated, with the group Gr(x, n) shifted in the Y direction by one pixel at a time. The calculation of the differential phase value is not limited to this. The group Gr(x, n) may be shifted, in the Y direction by two or more pixels as a unit each time, to calculate the differential phase value. In this case, it is preferable to shift a group by the number of pixels less than the Mpixels, constituting the group Gr(x, n), as a unit each time so as not to degrade the resolution of the differential phase image in the Y direction more than necessary.

In the first embodiment, the X-ray absorbing portions 22a of the second grid 22 extend in the Y direction. The extending direction of the X-ray absorbing portions 21a of the first grid 21 is tilted by the angle θ relative to the Y direction. Instead, the X-ray absorbing portions 21a of the first grid 21 may extend in the Y direction, and the extending direction of the X-ray absorbing portions 22a of the second grid 22 may be tilted by the angle θ relative to the Y direction. Alternatively, the X-ray absorbing portions 21a of the first grid 21 and the X-ray absorbing portions 22a of the second grid 22 may be tilted in opposite directions relative to the Y direction to form the angle θ. In the above-described first embodiment, the X-ray image detector 20 is disposed behind and close to the second grid 22. Thereby the X-ray image detector 20 detects the G2 image, produced by the second grid 22, of substantially equal magnification. Alternatively, the second grid 22 may be disposed away from the X-ray image detector 20. When "$L_3$" denotes a distance between the X-ray image detector 20 and the second grid 22 in the Z direction, the X-ray image detector 20 detects the G2 image enlarged with magnification R of a mathematical expression (14) below.

$$R = \frac{L_1 + L_2 + L_3}{L_1 + L_2} \tag{14}$$

In this case, a period T' of the moiré fringes detected by the X-ray image detector 20 is R times the moiré period T represented by the mathematical expression (6) (that is, T'=RT). Accordingly, the group Gr(x, n) is formed based on the moiré period T' in a similar manner.

In the above-described first embodiment, the differential phase value refers to the value represented by the mathematical expression (8) or (13), that is, a value representing the phase of the intensity modulated signal. Alternatively, the differential phase value may be multiplied by a constant, or a constant may be added to the differential phase value. The result obtained by the multiplication or the addition may be used as the differential phase value.

In the above-described first embodiment, the differential phase image is produced. In addition, an absorption image or a small angle scattering image may be produced. The absorption image is produced by obtaining an average of the intensity modulated signal shown in FIG. 6 by way of example. The small angle scattering image is produced by obtaining amplitude of the intensity modulated signal.

In the above-described first embodiment, the subject H is placed between the X-ray source 11 and the first grid 21. The subject H may be placed between the first grid 21 and the second grid 22.

In the first embodiment, the cone-shaped X-ray beams are emitted from the X-ray source 11. Alternatively, an X-ray source which emits parallel beams may be used. In this case, the first and second grids 21 and 22 are configured to substantially satisfy $p_2=p_1$, instead of the mathematical expression (1)

(Second Embodiment)

Figure 12:
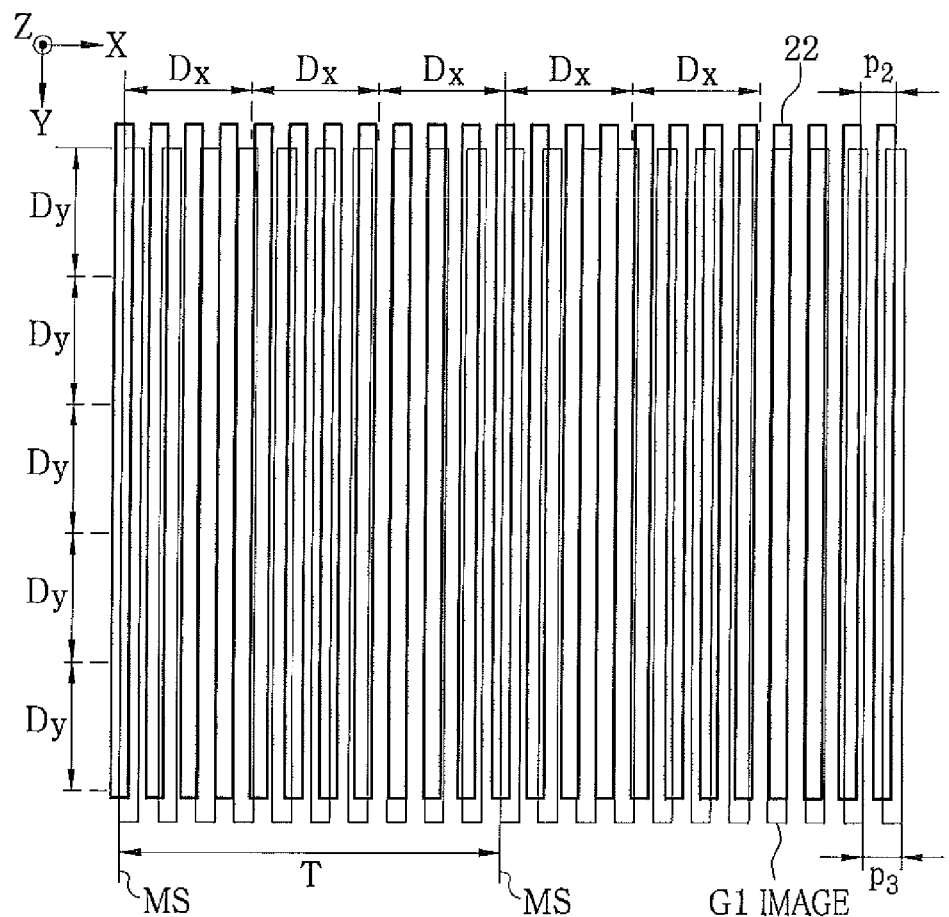
FIG. 12 is an explanatory view illustrating a positional relation between the first and second grids relative to the pixels of the X-ray image detector in the second embodiment.

Next, a second embodiment of the present invention is described. In the above-described first embodiment, the relative tilt of the first and second grids 21 and 22 in the direction within the grid plane causes moiré fringes MS in the G2 image. In the second embodiment, the first and second grids 21 and 22 are not tilted. Instead, a positional relation (the distances $L_1$ and $L_2$) between the first and second grids 21 and 22, or the grid pitches $p_1$ and $p_2$ of the first and second grids 21 and 22 are adjusted to be slightly different from the relation represented by the mathematical expression (1). Thereby, the moiré fringes MS occur in the G2 image as shown in FIG. 12.

The pattern period $p_3$ in the X direction of the G1 image at the position of the second grid 22 is slightly shifted from the grid pitch $p_2$ of the second grid 22. The moiré fringes MS have a period T in the X direction. The period T is represented by a mathematical expression (15) below.

$$T = \frac{p_2 p_3}{|p_2 - p_3|} \tag{15}$$

Figure 13:
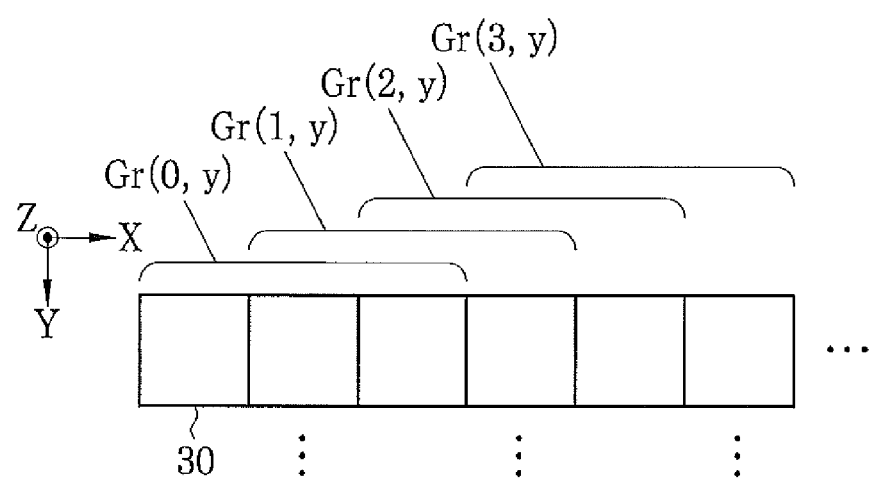
FIG. 13 is an explanatory view illustrating how to shift a group when the differential phase value is calculated in the second embodiment.

In this embodiment, as shown in FIG. 13, the differential phase image generator 40 calculates the differential phase value $\psi(x, y)$ based on the intensity modulated signal of each group Gr(n, y), with the group Gr(n, y) shifted (with "n" incremented) in the X direction by one pixel each time in each column of the pixels 30. The columns of the pixels 30 are arranged in the Y direction.

The differential phase value ψ(x, y) is calculated in a manner similar to the first embodiment. To be more specific, when the differential phase value ψ(x, y) is calculated using the calculation result of the determinant (7), a mathematical expression (16) is used instead of the mathematical expression (8), and a mathematical expression (17) is used instead of the mathematical expression (12).

$$\psi(n, y) = -\tan^{-1}\frac{a_2}{a_1} \qquad (16)$$

$$B(\delta_k) = \begin{pmatrix} \frac{1}{M}\sum_{k=0}^{M-1} I(n+k, y) \\ \frac{1}{M}\sum_{k=0}^{M-1} I(n+k, y)\cos\delta_k \\ \frac{1}{M}\sum_{k=0}^{M-1} I(n+k, y)\sin\delta_k \end{pmatrix} \qquad (17)$$

When the moiré period T is set to be an approximate integral multiple of the main pixel size Dx, the differential phase value ψ(x, y) is calculated with the use of a mathematical expression (18) below instead of the mathematical expression (13).

$$\psi(n, y) = -\tan^{-1}\frac{\sum_{k=0}^{M-1} I(n+k, y)\sin\delta_k}{\sum_{k=0}^{M-1} I(n+k, y)\cos\delta_k} \qquad (18)$$

In this embodiment, similar to the first embodiment, the number M of the pixels in one group Gr(n, y) may not necessarily be equivalent to the number ν of the pixels included in the single moiré period T or N times the moiré period T. The number M may be less than the number ν of the pixels included in the single moiré period T. The differential phase value may be calculated, with the group Gr(n, y) shifted in the X direction by two or more pixels as a unit each time. Configuration and operation other than those described above are similar to those in the first embodiment.

In this embodiment, note that the distance between the X-ray image detector 20 and the second grid 22 may be set to $L_3$. In this case, the group Gr(n, y) is formed based on the moiré period T'. The moiré period T' is calculated by multiplying the moiré period T represented by the mathematical expression (15) by the magnification R represented by the mathematical expression (14).

The moiré fringes with a period in a direction not parallel with either the X direction or the Y direction may occur in the G2 image when the relative tilt of the first and second grids 21 and 22 in the direction within the grid surface and a shift in the grid pitch or the positional relation between the first and second grids 21 and 22 described in the above-described first embodiment occur at the same time. In this case, the moiré fringes have components in X and Y directions. Hence, the differential phase image is produced using one of the methods described in the first and second embodiments. A group may be formed with the pixels 30 arranged in an oblique direction, not parallel with either the X direction or the Y direction, to produce the differential phase image in a manner similar to the above.

(Third Embodiment)

Next, a third embodiment of the present invention is described. In the first and second embodiments, the X-ray source 11 has the single focal point. In the third embodiment, as shown in FIG. 14, a multi-slit (source grid) 23 disclosed in WO2006/131235 or the like is disposed in front of the X-ray source 11 on the emission side. Similar to the first and second grids 21 and 22, the multi-slit 23 has a plurality of X-ray absorbing portions 23a and a plurality of X-ray transmitting portions 23b, extending in the Y direction and arranged alternately in the X direction. The grid pitch $p_0$ of the multi-slit 23 is set to substantially satisfy a mathematical expression (19) below, where "$L_0$" denotes a distance between the multi-slit 23 and the first grid 21.

$$p_0 = \frac{L_0}{L_2}p_2 \qquad (19)$$

The radiation from the X-ray source 11 is dispersed in the Y direction such that the each X-ray transmitting portion 23b functions as the small (narrow) X-ray focal point. The radiation applied from the each X-ray transmitting portion 23b and passed through the first grid 21 forms the G1 image. The G1 images are overlapped with each other at the position of the second grid 22 to form the G2 image. This increases the contrast of the G2 image and improves accuracy in the calculation of the differential phase image.

The configuration and operation other than those described above are the same as those in the first or second embodiments. Because each X-ray transmitting portion 23b of the multi-slit 23 functions as the X-ray focal point in this embodiment, the distance $L_0$ replaces the distance $L_1$ in the mathematical expression (1).

In this embodiment, note that the distance between the X-ray image detector 20 and the second grid 22 may be set to $L_3$. In this case, the group Gr(x, n) or the group Gr(n, y) may be formed based on the moiré period T'. The moiré period T' is obtained by multiplying the moiré period T, represented by the mathematical expression (6) or (15), by the magnification R of the mathematical expression (14). Note that even if the multi-slit 23 is used, the G2 image produced by the second grid 22 is enlarged around the origin, being the X-ray focal point 11a of the X-ray source 11. The G2 image is enlarged in proportion to the distance between the X-ray focal point 11a and the X-ray image detector 20. Hence, as for the magnification R of the G2 image, the mathematical expression (14) is used as it is (without replacing the $L_1$ with the $L_0$).

(Fourth Embodiment)

Next, a fourth embodiment of the present invention is described. In the first to third embodiments, the first grid 21 projects the incident X-rays in the geometrical-optical manner without diffraction. In an X-ray imaging apparatus of the fourth embodiment, the first grid 21 produces Talbot effect as described in Japanese Patent Laid-Open Publication No. 2008-200361 or the like. To produce the Talbot effect with the first grid 21, an X-ray source of a small focal point is used to increase spatial interference of the X-rays or the above-described multi-slit 23 is used to reduce the size of the focal point.

When the first grid 21 produces the Talbot effect, a self image (the G1 image) of the first grid 21 is formed downstream from the first grid 21 at a Talbot distance $Z_m$ away from the first grid 21. In this embodiment, the distance $L_2$ between the first grid 21 and the second grid 22 needs to be set to the Talbot distance $Z_m$. Note that a phase grid may be used as the first grid 21.

Configuration and operation other than those described in this embodiment are the same as those described in the first, second, or third embodiments.

When the first grid 21 is the absorption grid and the X-ray source 11 emits the cone-shaped X-ray beams, the Talbot distance $Z_m$ is represented by a mathematical expression (20) below, where "m" is a positive integer. In this case, the grid pitches $p_1$ and $p_2$ are set to substantially satisfy the mathematical expression (1) (Note that when the multi-slit 23 is used, the distance $L_0$ replaces the distance $L_1$).

$$Z_m = m \frac{p_1 p_2}{\lambda} \quad (20)$$

When the first grid 21 is the phase grid that modulates the phase by $\pi/2$, and the X-ray source 11 emits the cone-shaped X-ray beams, the Talbot distance $Z_m$ is represented by a mathematical expression (21), where "m" is "0" or a positive integer. In this case, the grid pitches $p_1$ and $p_2$ are set to substantially satisfy the mathematical expression (1) (note that when the multi-slit 23 is used, the distance $L_0$ replaces the distance $L_1$).

$$Z_m = \left(m + \frac{1}{2}\right) \frac{p_1 p_2}{\lambda} \quad (21)$$

When the first grid 21 is the phase grid that modulates the phase by n and the X-ray source 11 emits the cone-shaped X-ray beams, the Talbot distance $Z_m$ is represented by a mathematical expression (22) below, where "m" is "0" or a positive integer.

In this case, the pattern period of the G1 image is 1/2 times the grid period of the first grid 21. Hence, the grid pitches $p_1$ and $p_2$ are set to substantially satisfy a mathematical expression (23) below (note that when the multi-slit 23 is used, the distance $L_0$ replaces the distance $L_1$).

$$Z_m = \left(m + \frac{1}{2}\right) \frac{p_1 p_2}{2\lambda} \quad (22)$$

$$p_2 = \frac{L_1 + L_2}{L_1} \frac{p_1}{2} \quad (23)$$

When the first grid 21 is the absorption grid, and the X-rays from the X-ray source 11 are parallel beams, the Talbot distance $Z_m$ is represented by a mathematical expression (24) below, where "m" is a positive integer. In this case, the grid pitches $p_1$ and $p_2$ are set to substantially satisfy $p_2=p_1$.

$$Z_m = m \frac{p_1^2}{\lambda} \quad (24)$$

When the first grid 21 is the phase grid that modulates the phase by $\pi/2$, and the X-rays from the X-ray source 11 are parallel beams, the Talbot distance $Z_m$ is represented by a mathematical expression (25) below, where "m" is "0" or a positive integer. In this case, the grid pitches $p_1$ and $p_2$ are set to substantially satisfy $p_2=p_1$.

$$Z_m = \left(m + \frac{1}{2}\right) \frac{p_1^2}{\lambda} \quad (25)$$

When the first grid 21 is the phase grid that modulates the phase by $\pi$, and the X-rays from the X-ray source 11 are the parallel beams, the Talbot distance $Z_m$ is represented by a mathematical expression (26) below, where "m" is "0" or a positive integer.

In this case, the pattern period of the G1 image is 1/2 times the grid period of the first grid 21. Hence, the grid pitches $p_1$ and $p_2$ are set to substantially satisfy $p_2=p_1/2$.

$$Z_m = \left(m + \frac{1}{2}\right) \frac{p_1^2}{4\lambda} \quad (26)$$

(Fifth Embodiment)

Next, a fifth embodiment of the present invention is described. In the above-described first to fourth embodiments, the X-ray image detector 20 in which a charge is electrically read out from the pixel 30 through the TFT is described. The fifth embodiment employs an X-ray image detector of an optical reading system in which a charge is read out by scanning with linear reading light.

Figure 15:
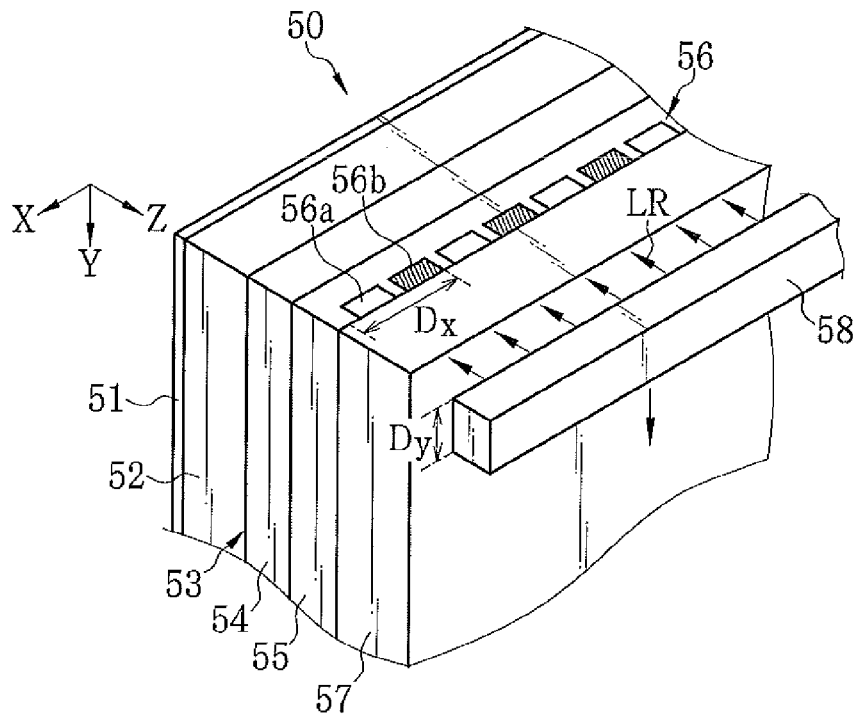
FIG. 15 is a schematic perspective view illustrating a structure of the X-ray image detector according to a fifth embodiment.

In FIG. 15, an X-ray image detector 50 is provided with a first electrode layer 51, a recording photoconductive layer 52, a charge transport layer 54, a reading photoconductive layer 55, and a second electrode layer 56, in this order from the top. The first electrode layer 51 passes the X-rays. The recording photoconductive layer 52 receives the X-rays, passed through the first electrode layer 51, to generate a charge. The charge transport layer 54 acts as an insulator to the charge of a polarity out of the charges generated in the recording photoconductive layer 52 and as a conductor to the charge of the opposite polarity. The reading photoconductive layer 55 receives reading light LR to generate a charge.

A capacitor portion 53 is formed at around an interface between the recording photoconductive layer 52 and the charge transport layer 54. The capacitor portion 53 stores the charge generated in the recording photoconductive layer 52. Note that the layers are in the above-mentioned order with the second electrode layer 56 formed on a glass substrate 57.

The first electrode layer 51 passes the X-rays. The first electrode layer 51 is, for example, a NESA film ($SnO_2$), ITO (Indium Tin Oxide), IZO (Indium Zinc Oxide), or IDIXO (Idemitsu Indium X-metal Oxide, a product of Idemitsu Kosan Co., Ltd.), being an amorphous light-transmissive oxide film, with the thickness of 50 nm to 200 nm. Al or Au with the thickness of 100 nm may be used.

Any substance which receives the X-rays and generates the charge may be used as the recording photoconductive layer 52. In this embodiment, a substance containing amorphous selenium as a main component is used, having advantage in relatively high quantum efficiency and high dark resistance. The appropriate thickness of the recording photoconductive layer 52 is from 10 μm to 1500 μm. For mammography, the thickness of the recording photoconductive layer 52 is preferably from 150 μm to 250 μm. For general radiography, the thickness of the recording photoconductive layer 52 is preferably from 500 μm to 1200 μm.

The greater a difference between mobility of the charge charged in the first electrode layer 51 and mobility of the charge of reverse polarity, the better the charge transport layer 54, when the X-ray image is recorded. For example, an organic compound such as poly (N-vinyl carbazole) (PVK), N,N'-diphenyl-N, N'-bis(3-methylphenyl)-[1,1'-biphenyl]-4, 4'-diamine (TPD), or discotic liquid crystal, polymer (polycarbonate, polystyrene, or PVK) dispersion of TPD, and a semiconductor material such as a-Se or $As_2Se_3$, doped with 10 ppm to 200 ppm of Cl, are suitable. The appropriate thickness of the charge transport layer 54 is of the order of 0.2 μm to 2 μm.

Any substance which receives the reading light LR and exhibits conductivity may be used as the reading photoconductive layer 55. It is suitable to use a photoconductive substance having at least one of the following as a main component: a-Se, Se—Te, Se—As—Te, metal-free phthalocyanine, metal phthalocyanine, MgPc (Magnesium phthalocyanine), VoPc (phase II of Vanadyl phthalocyanine), and CuPc (Cupper phthalocyanine), for example. The appropriate thickness of the reading photoconductive layer 55 is of the order of 5 μm to 20 μm.

The second electrode layer 56 has a plurality of transparent linear electrodes 56a and a plurality of light-shielding linear electrodes 56b. The transparent linear electrodes 56a pass the reading light LR. The light-shielding linear electrodes 56b block the reading light LR. The transparent linear electrodes 56a and the light-shielding linear electrodes 56b extend linearly from end to end of an image forming area of the X-ray image detector 50. The transparent linear electrodes 56a and the light-shielding linear electrodes 56b are arranged alternately and parallel to each other at regular intervals.

The transparent linear electrode 56a is made from a material which has conductivity and transmits the reading light LR, for example, ITO, IZO, or IDIXO, similar to the first electrode layer 51. The thickness of the transparent linear electrode 56a is of the order of 100 nm to 200 nm.

The light-shielding linear electrode 56b is made from a material which has conductivity and blocks the reading light LR.

For example, a combination of the above-described transparent conductive material and a color filter is used. The thickness of the transparent conductive material is of the order of 100 nm to 200 nm.

In the X-ray image detector 50, the above-described main pixel size Dx is determined by a pair of the transparent linear electrode 56a and the light-shielding linear electrode 56b adjacent to each other.

The X-ray image detector 50 comprises a linear reading light source 58 that extends in the direction (X direction) orthogonal to the extending direction of the transparent linear electrodes 56a and the light-shielding linear electrodes 56b. The linear reading light source 58 is composed of a light source such as an LED (Light Emitting Diode) or an LD (Laser Diode) and an optical system. The linear reading light source 58 emits linear reading light LR to the glass substrate 57. A moving mechanism (not shown) moves the linear reading light source 58 in the extending direction (Y direction) of the transparent linear electrodes 56a and the light-shielding linear electrodes 56b. The charge is read out using the linear reading light from the linear reading light source 58. A width of the linear reading light source 58 in the Y direction determines the above-described sub-pixel size Dy. In this embodiment, the width of the linear reading light source 58 in the Y direction is reduced to reduce the sub-pixel size Dy. Thereby, the resolution of the differential phase image in the sub-pixel direction increases.

Figure 16:
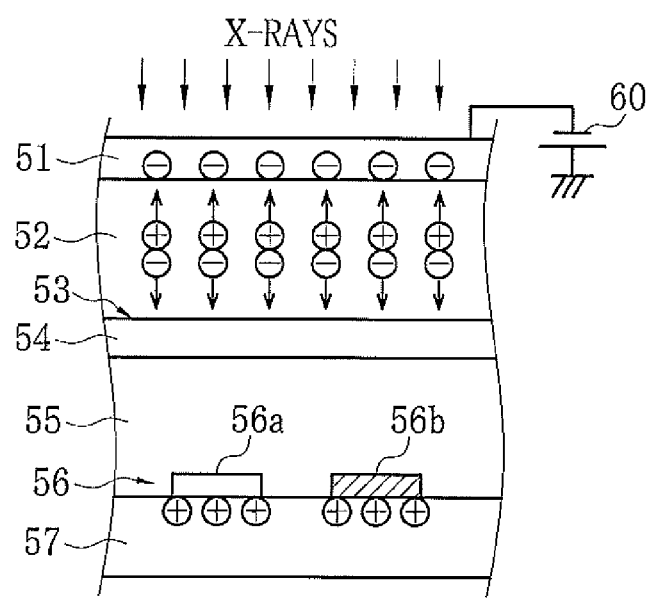
FIG. 16 is an explanatory view illustrating an operation of the X-ray image detector according to the fifth embodiment.

Next, image detection and reading with the use of the X-ray image detector 50 are described. First, as shown in FIG. 16, a high voltage power supply 60 applies negative voltage to the first electrode layer 51 of the X-ray image detector 50. In this state, the X-rays, emitted from the X-ray source 11 and passed through the first and second grids 21 and 22, are incident as the G2 image on the X-ray image detector 50 from the first electrode layer 51 side.

Figure 17:
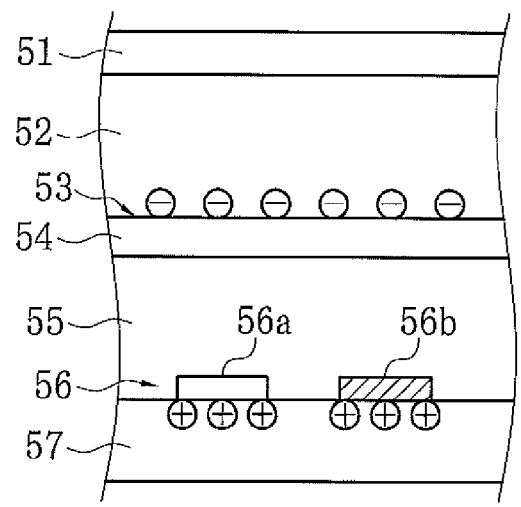
FIG. 17 is an explanatory view illustrating an operation of the X-ray image detector according to the fifth embodiment.

The X-rays incident on the X-ray image detector 50 pass through the first electrode layer 51 and then are incident on the recording photoconductive layer 52. Thereby, the recording photoconductive layer 52 generates charge pairs. Of the charge pairs, a positive charge (a positive hole) bonds with a negative charge (an electron) charged in the first electrode layer 51 to cancel each other. As shown in FIG. 17, the negative charge, being latent image charge, is accumulated in the capacitor portion 53 formed at the interface between the recording photoconductive layer 52 and the charge transport layer 54.

Figure 18:
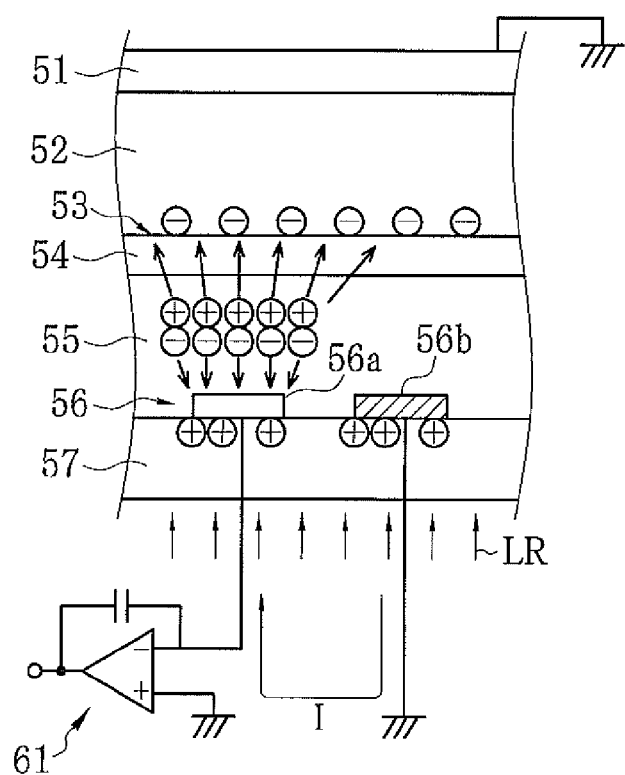
FIG. 18 is an explanatory view illustrating an operation of the X-ray image detector according to the fifth embodiment.

Next, as shown in FIG. 18, the linear reading light LR from the linear reading light source 58 is applied from the glass substrate 57 side in a state that the first electrode layer 51 is grounded. The reading light LR passes through the glass substrate 57 and the transparent linear electrode 56a. Then the reading light LR is incident on the reading photoconductive layer 55. Thereby, the positive charge is generated in the reading photoconductive layer 55. The positive charge passes through the charge transport layer 54 and bonds with the latent image charge in the capacitor portion 53, while the negative charge bonds with the positive charge charged in the light-shielding linear electrode 56b through an integrating amplifier 61 connected to the transparent linear electrode 56a.

When the negative charge generated in the reading photoconductive layer 55 bonds with the positive charge charged in the light-shielding linear electrode 56b, a current "I" flows in the integrating amplifier 61. The current I is integrated and then outputted as an image signal.

Thereafter, the linear reading light source 58 moves in the Y direction with a moving pitch of the sub-pixel size Dy. After each move of the linear reading light source 58 with the moving pitch, the above-described charge reading operation is performed. The image signal is detected from each reading line to which the linear reading light LR is applied. The image signal of each reading line is outputted successively from the integrating amplifier 61.

The A/D converter and the correction circuit (both not shown) perform processing on the image signal outputted from the integrating amplifier 61, in a manner similar to the first embodiment. Thereby digital image data is produced. Namely, the image data similar to the first embodiment is obtained. The image data is inputted to the memory 13. The X-ray image detector 50 is applicable to any of the first to fourth embodiments. Other configuration and operation of this embodiment are the same as those in one of the first to fourth embodiments.

The above-described embodiments may be used in combination as long as it does not have any contradictions. The present invention may be applied to a radiation imaging apparatus of industrial use, or the like, in addition to the radiation imaging apparatus for medical diagnosing. Instead of the X-rays, gamma rays or the like may be used as the radiation.

Various changes and modifications are possible in the present invention and may be understood to be within the present invention.

What is claimed is:

1. A radiation imaging apparatus comprising:
a radiation source for emitting radiation;
a first grid for passing the radiation and producing a first periodic pattern image;

a second grid for partly blocking the first periodic pattern image to produce a second periodic pattern image with moiré fringes;

a radiation image detector for detecting the second periodic pattern image with the use of pixels, arranged in two dimensions, and producing image data; and a differential phase image generator for grouping M number of pixels, arranged in a predetermined direction, as a group and calculating a phase of an intensity modulated signal, with the group shifted in the predetermined direction by a number of the pixels less than the M number of pixels each time, to produce a differential phase image, the intensity modulated signal being composed of pixel values of the pixels in the each group.

2. The radiation imaging apparatus of claim 1, wherein the differential phase image generator calculates the phase of the intensity modulated signal, with the group shifted in the predetermined direction by one pixel each time, and the intensity modulated signal is composed of the pixel values of the pixels in the each group.

3. The radiation imaging apparatus of claim 2, wherein the predetermined direction is a direction substantially orthogonal to the moiré fringes.

4. The radiation imaging apparatus of claim 3, wherein the number of the pixels constituting the group corresponds to an integral multiple of a period of the moiré fringes.

5. The radiation imaging apparatus of claim 4, wherein the number of the pixels constituting the group corresponds to the one period of the moiré fringes.

6. The radiation imaging apparatus of claim 3, wherein the number of the pixels constituting the group is less than the number of the pixels corresponding to one period of the moiré fringes.

7. The radiation imaging apparatus of claim 3, wherein the moiré fringes are produced by arranging the second grid with a tilt in a direction within a grid surface relative to the first grid, and the moiré fringes are substantially orthogonal to grid directions of the first and second grids.

8. The radiation imaging apparatus of claim 3, wherein the moiré fringes are produced by adjusting a positional relation between the first and second grids in an opposing direction or adjusting a grid pitch or grid pitches of the first and second grids, and the moiré fringes are substantially parallel with a grid direction of the first and second grids.

9. The radiation imaging apparatus of claim 3, wherein the moiré fringes are produced by arranging the second grid with a tilt in a direction within a grid surface relative to the first grid and adjusting a positional relation between the first and second grids in an opposing direction or adjusting a grid pitch or grid pitches of the first and second grids, and the moiré fringes are neither orthogonal nor parallel to grid directions of the first and second grids.

10. The radiation imaging apparatus of claim 3, further comprising a phase contrast image generator for performing an integrating process on the differential phase image in a direction substantially orthogonal to a grid direction or grid directions of the first and second grids and producing a phase contrast image.

11. The radiation imaging apparatus of claim 3, further comprising:

correction image storage for storing a differential phase image, produced by the differential phase image generator in absence of a subject, as a correction image; and a correction processor for subtracting the correction image, stored in the correction image storage, from a differential phase image produced by the differential phase image generator in presence of the subject.

12. The radiation imaging apparatus of claim 11, further comprising a phase contrast image generator for performing an integrating process on a corrected differential phase image, corrected by the correction processor, in a direction substantially orthogonal to a grid direction or grid directions of the first and second grids and producing a phase contrast image.

13. The radiation imaging apparatus of claim 3, wherein the first grid is an absorption grid for projecting the incident radiation in a geometrical-optical manner to the second grid and producing the first periodic pattern image.

14. The radiation imaging apparatus of claim 3, wherein the first grid is an absorption grid or a phase grid for allowing the incident radiation to cause Talbot effect and producing the first periodic pattern image.

15. The radiation imaging apparatus of claim 3, further comprising a multi-slit for partly blocking the radiation emitted from the radiation source and dispersing a focus.

16. The radiation imaging apparatus of claim 3, wherein the radiation image detector is a radiation image detector of an optical reading system in which a charge is read out from each pixel by scanning a linear reading light source in the predetermined direction and image data is produced, and the linear reading light source extends in a direction orthogonal to the predetermined direction.

17. An image processing method for use in a radiation imaging apparatus comprising a radiation source for emitting radiation, a first grid for passing the radiation and producing a first periodic pattern image, a second grid for partly blocking the first periodic pattern image to produce a second periodic pattern image with moiré fringes, and a radiation image detector for detecting the second periodic pattern image with the use of pixels, arranged in two dimensions, and producing image data, the image processing method comprising the step of:

grouping M number of pixels, arranged in a predetermined direction, as a group and calculating a phase of an intensity modulated signal, with the group shifted in the predetermined direction by a number of the pixels less than the M number of pixels each time, to produce a differential phase image, the intensity modulated signal being composed of pixel values of the pixels in the each group.

* * * * *